(12) United States Patent
Kim et al.

(10) Patent No.: US 9,649,164 B2
(45) Date of Patent: May 16, 2017

(54) SURGICAL ROBOT SYSTEM AND SURGICAL ROBOT CONTROL METHOD

(71) Applicant: HYUNDAI HEAVY INDUSTRIES CO., LTD., Ulsan (KR)

(72) Inventors: Sung Min Kim, Towson, MD (US); Sang Hun Lee, Seoul (KR); Sung Hyun Jung, Seoul (KR)

(73) Assignee: Hyundai Heavy Industries Co., Ltd., Ulsan (KR)

( * ) Notice: Subject to any disclaimer, the term of this patent is extended or adjusted under 35 U.S.C. 154(b) by 24 days.

(21) Appl. No.: 14/413,686

(22) PCT Filed: Jul. 10, 2013

(86) PCT No.: PCT/KR2013/006141
§ 371 (c)(1),
(2) Date: Jan. 8, 2015

(87) PCT Pub. No.: WO2014/010941
PCT Pub. Date: Jan. 16, 2014

(65) Prior Publication Data
US 2015/0202014 A1 Jul. 23, 2015

(30) Foreign Application Priority Data

Jul. 10, 2012 (KR) .................. 10-2012-0075283
Oct. 18, 2012 (KR) .................. 10-2012-0116277
Jul. 3, 2013 (KR) .................. 10-2013-0077488

(51) Int. Cl.
*A61B 19/00* (2006.01)
*B25J 9/16* (2006.01)
(Continued)

(52) U.S. Cl.
CPC .......... *A61B 19/2203* (2013.01); *A61B 34/30* (2016.02); *A61B 34/32* (2016.02);
(Continued)

(58) Field of Classification Search
CPC .. A61B 19/22013; A61B 34/32; B25J 9/1676; B25J 9/02; B25J 9/1674; B25J 9/1666
See application file for complete search history.

(56) References Cited

U.S. PATENT DOCUMENTS 7,035,716 B2 *  4/2006  Harris ............... B25J 9/1689
                                                318/568.1
7,996,110 B2 *  8/2011  Lipow ............... G09B 23/28
                                                318/568.11
(Continued)

FOREIGN PATENT DOCUMENTS

JP    2007029232 A    2/2007
JP    2008018172 A    1/2008
(Continued)

OTHER PUBLICATIONS

Choi Seung Wook, Won Jong Seok, Lee Min Kyl, Jang Bae Sang, Lee Woo Jyoung; "Surgical Robot System and Control Method Thereof"; Aug. 19, 2010; Abstract of KR20100091784 (A); www.espacenet.com.

(Continued)

*Primary Examiner* — Nicholas Kiswanto
(74) *Attorney, Agent, or Firm* — Andrew D. Fortney; Central California IP Group, P.C.

(57) ABSTRACT

Disclosed are a surgical robot system and a surgical robot control method. The surgical robot system includes a surgical tool configured to perform surgery on each of a plurality of procedure regions in a surgical region which is divided into the plurality of procedure regions, a robot arm on which the surgical tool is mounted, and a driver configured to operate the robot arm. The present invention adjusts a speed at which a surgical robot moves, based on a risk level which is set for a procedure region, and thus enhances a stability of surgery performed by the surgical robot and (Continued)

moreover decreases a degree to which the surgery is delayed, thereby reducing pain and inconvenience caused to an operator and a patient.

12 Claims, 5 Drawing Sheets

(51) Int. Cl.
    A61B 34/32    (2016.01)
    A61B 34/30    (2016.01)
    A61B 34/00    (2016.01)
    A61B 34/10    (2016.01)
(52) U.S. Cl.
    CPC ............. *A61B 34/77* (2016.02); *B25J 9/1676* (2013.01); *A61B 2034/107* (2016.02); *G05B 2219/40418* (2013.01)

(56) References Cited

U.S. PATENT DOCUMENTS

| | | | | |
|---|---|---|---|---|
| 8,184,880 | B2* | 5/2012 | Zhao | G06K 9/6211 345/419 |
| 8,506,555 | B2* | 8/2013 | Ruiz Morales | B25J 9/041 606/1 |
| 8,571,628 | B2* | 10/2013 | Kang | A61N 1/372 600/407 |
| 9,002,426 | B2* | 4/2015 | Quaid | A61B 17/1764 600/407 |
| 9,119,655 | B2* | 9/2015 | Bowling | A61B 34/32 |
| 2011/0276058 | A1 | 11/2011 | Choi et al. | |
| 2011/0306985 | A1 | 12/2011 | Inoue et al. | |
| 2016/0062475 | A1* | 3/2016 | Gombert | G06F 3/0338 74/471 R |

FOREIGN PATENT DOCUMENTS

| | | |
|---|---|---|
| JP | 2010240067 A | 10/2010 |
| JP | 2011254975 A | 12/2011 |
| KR | 20100091784 A | 8/2010 |
| KR | 20100112310 A | 10/2010 |
| KR | 20110024026 A | 3/2011 |
| KR | 20110059587 A | 6/2011 |

OTHER PUBLICATIONS

Jeong Ji Hoon, Jeon Jean Hong, Song Dong Ryul; "Method and System for Controlling Microsurgery Robot"; Oct. 19, 2010; Abstract of KR20100112310 (A); www.espacenet.com.
Kim Young Soo, Yi Byung Ju, Kim Sung Min, Jang Jong Seong; "Medical Robot System and Method for Controlling the Same"; Mar. 9, 2011; Abstract of KR20110024026 (A); www.espacenet.com.
Choi Seung Wook, Lee Min Kyu; "Surgical Robot System and Motion Restriction Control Method Thereof"; Jun. 2, 2011; Abstract of KR20110059587 (A); www.espacenet.com.
"Surgery Support System"; Dec. 22, 2011; Abstract of JP2011254975 (A); 2 pgs.; www.espacenet.com.
English translation of International Search Report, International Application No. PCT/KR2013/006141; Oct. 8, 2013; 2 pgs.
Takeshi Mochizuki et al.; "Medical Navigation System"; Bibliographic Data of JP2010240067 (A); Oct. 28, 2010; http://worldwide.espacenet.com.
Hidekazu Nakamoto et al.; "Surgery Supporting System"; Bibliographic Data of JP2008018172 (A); Jan. 31, 2008; 2 pgs.; http://worldwide.espacenet.com.
Hiroki Taniguchi; "System for Supporting Endoscopic Operation"; Bibliographic Data of JP2007029232 (A); Feb. 8, 2007; http://worldwide.espacenet.com.

* cited by examiner

SURGICAL ROBOT SYSTEM AND SURGICAL ROBOT CONTROL METHOD

BACKGROUND

Field of the Invention

The present invention relates to a surgical robot system and a surgical robot control method which are used to perform medical surgery.

Discussion of the Related Art

Surgery is an operation which cuts or incises skin, a mucous membrane, or the other tissue with a medical instrument, or performs the other manipulation, thereby treating a disease. Examples of surgery include various kinds of surgeries such as minimal invasive surgery including laparoscopic surgery, joint replacement surgery, prostatectomy, etc., based on a diseased part. For example, minimal invasive surgery is a surgical technique that inserts a surgical instrument into a body of a patient through a small incised part, and minimizes incision for surgery.

Recently, a surgical robot system that performs surgery with a surgical robot so as to enhance an accuracy, a precision, and a delicacy of the surgery is being actively developed. For example, in the Da Vinci surgical robot, a robot arm which is directly inserted into a body of a patient may perform surgery by operating like an operator's hand. Technology relevant to a background of the surgical robot system is disclosed in Korean Patent Publication No. 10-2005-0100147 (published on Oct. 18, 2005) and Korean Patent Publication No. 10-2010-0048789 (published on May 11, 2010).

Here, a blood vessel, an organ, etc. (hereinafter referred to as a risk object) which exert a great influence on a patient's life like aorta, a heart, and lungs may be located in a surgical region including a diseased part, and when surgery is performed on a surgical region close to the risk object, it is required to perform more accurate and precise surgery in comparison with the other surgical regions. However, a related art surgical robot system always performs surgery on a whole region of a surgical region through the same operation irrespective of a risk object located in the surgical region, and for this reason, there is a risk of causing a serious medical accident.

SUMMARY

Accordingly, the present invention is directed to provide a surgical robot system and a surgical robot control method that substantially obviate one or more problems due to limitations and disadvantages of the related art.

An aspect of the present invention is directed to provide a surgical robot system and a surgical robot control method, which decrease a risk of causing a medical accident in a process of performing surgery with a surgical robot.

Additional advantages and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these and other advantages and in accordance with the purpose of the invention, as embodied and broadly described herein, there is provided a surgical robot system including: a surgical tool configured to perform surgery on each of a plurality of procedure regions in a surgical region which is divided into the plurality of procedure regions; a robot arm on which the surgical tool is mounted; and a driver configured to operate the robot arm, wherein the driver adjusts an operating speed at which the robot arm operates, based on a risk level which is set for a procedure region in which the surgical tool is disposed.

In another aspect of the present invention, there is provided a surgical robot control method including: when a procedure region in which a surgical robot is disposed is changed in a surgical region which is divided into a plurality of procedure regions, checking a risk level which is set for the changed procedure region, based on a risk object located in the surgical region; determining whether the risk level is changed according to the procedure region being changed; and when whether the risk level is changed is determined, controlling the surgical robot for an operating speed, at which the surgical robot operates, to be adjusted based on the risk level.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiments of the invention and together with the description serve to explain the principle of the invention. In the drawings.

DETAILED DESCRIPTION OF THE INVENTION

Reference will now be made in detail to the exemplary embodiments of the present invention, examples of which are illustrated in the accompanying drawings. Wherever possible, the same reference numbers will be used throughout the drawings to refer to the same or like parts.

Hereinafter, exemplary embodiments of a surgical robot system according to the present invention will be described in detail with reference to the accompanying drawings.

Figure 1:
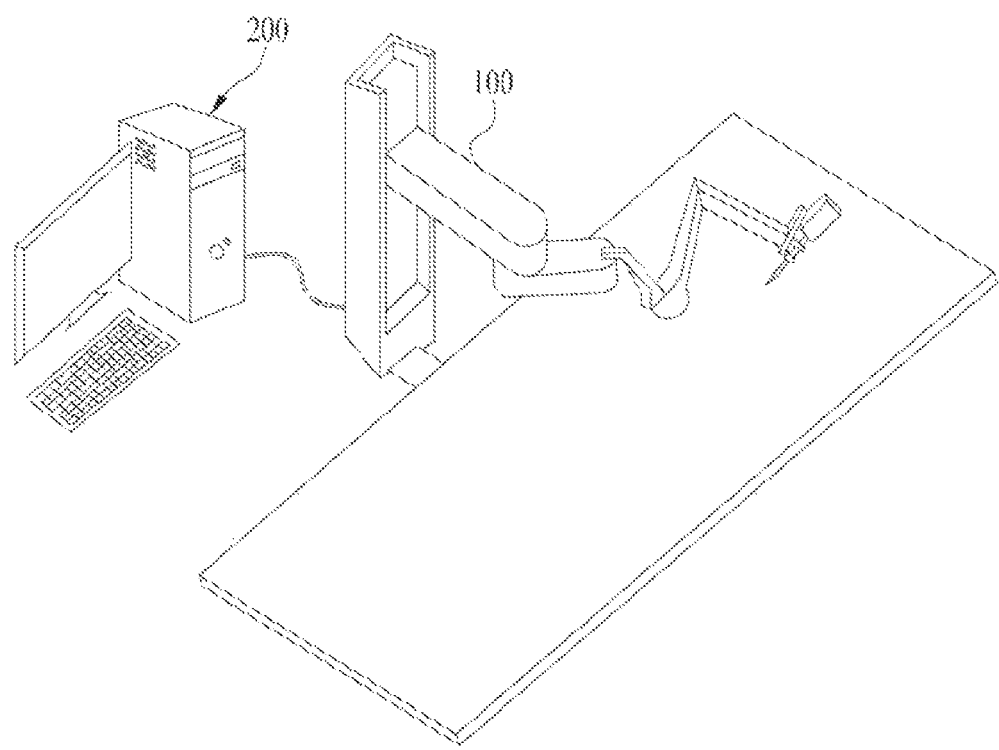
FIG. 1 is a schematic perspective view of a surgical robot system according to an embodiment of the present invention.
Figure 2:
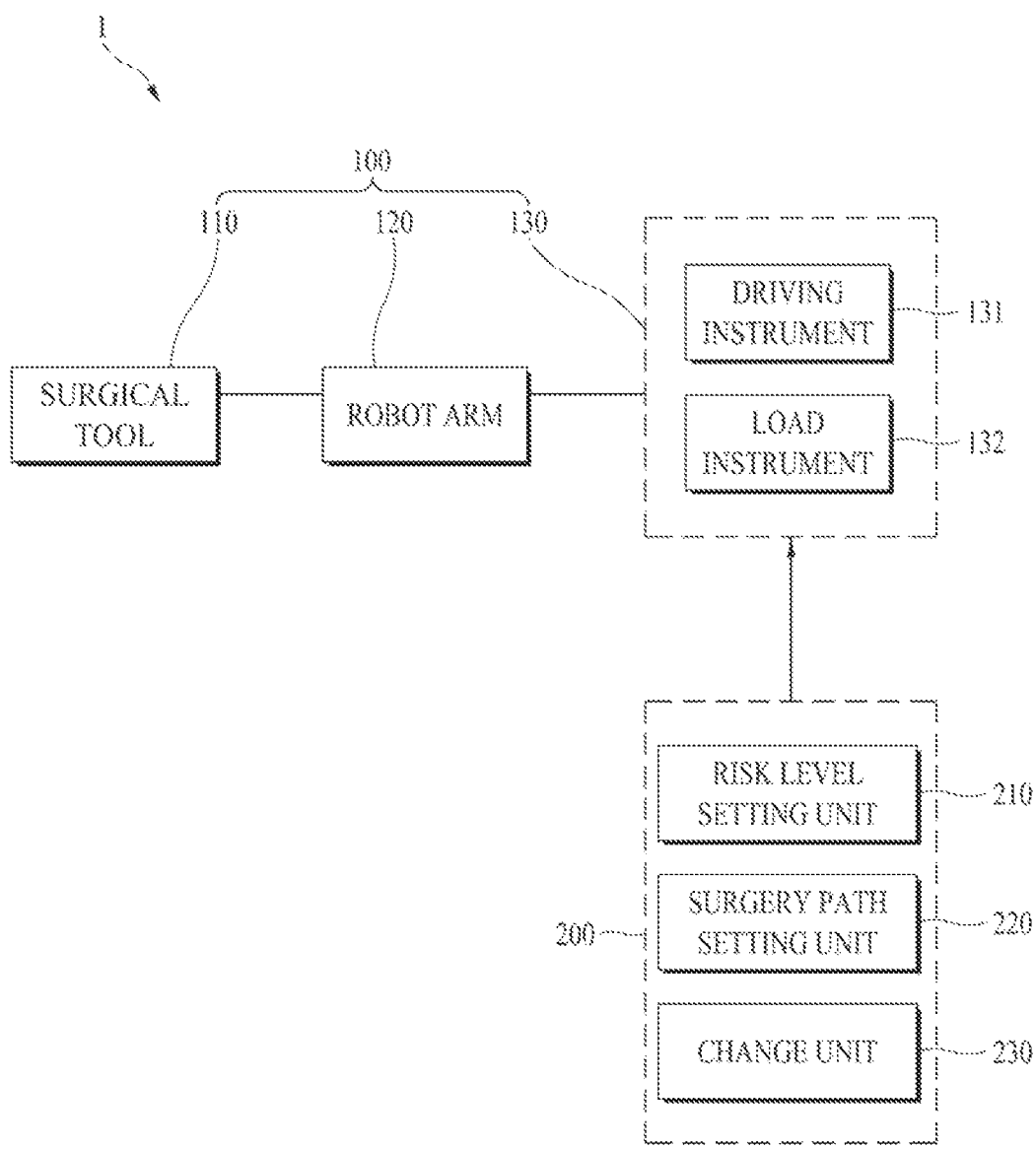
FIG. 2 is a schematic block diagram of a surgical robot system according to an embodiment of the present invention.
Figure 3:
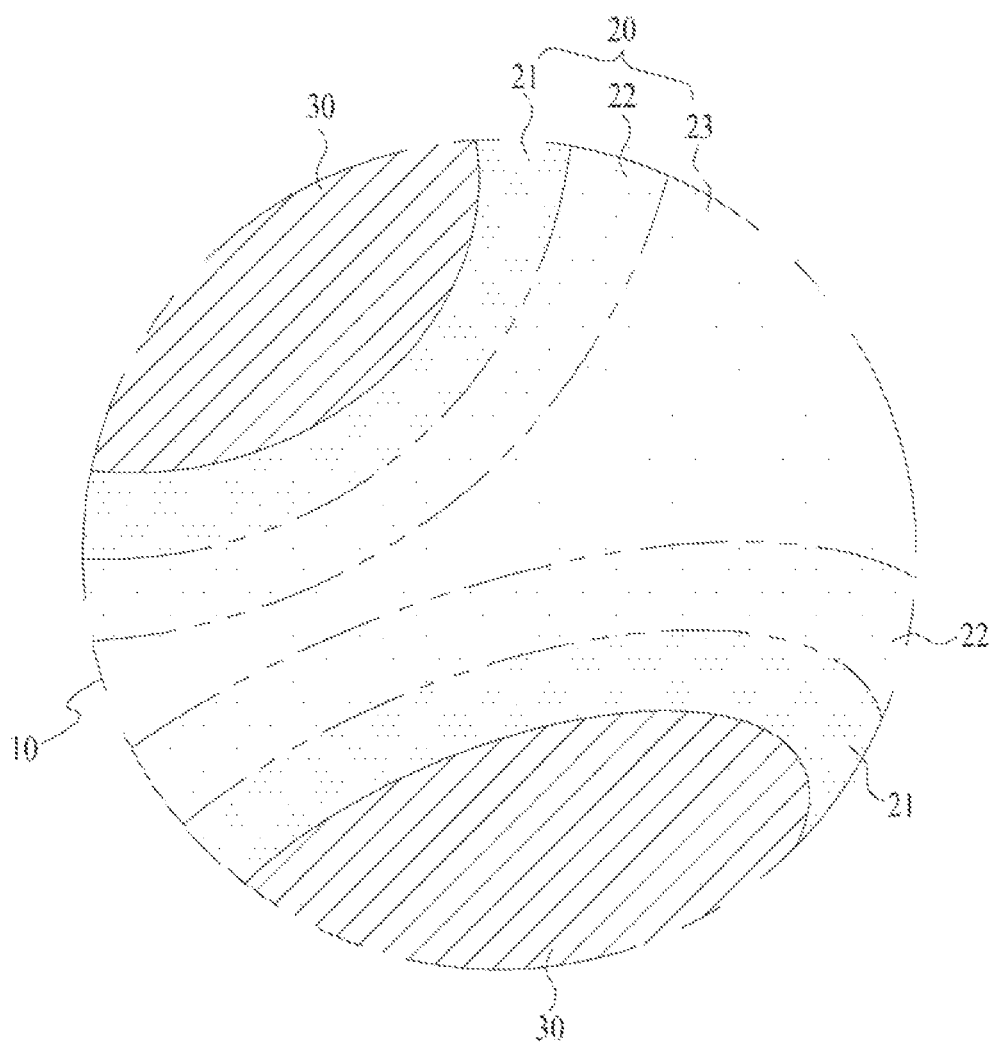
FIG. 3 is a conceptual diagram illustrating an example in which a risk level is set based on a surgical region, in a surgical robot system according to an embodiment of the present invention.
Figure 4:
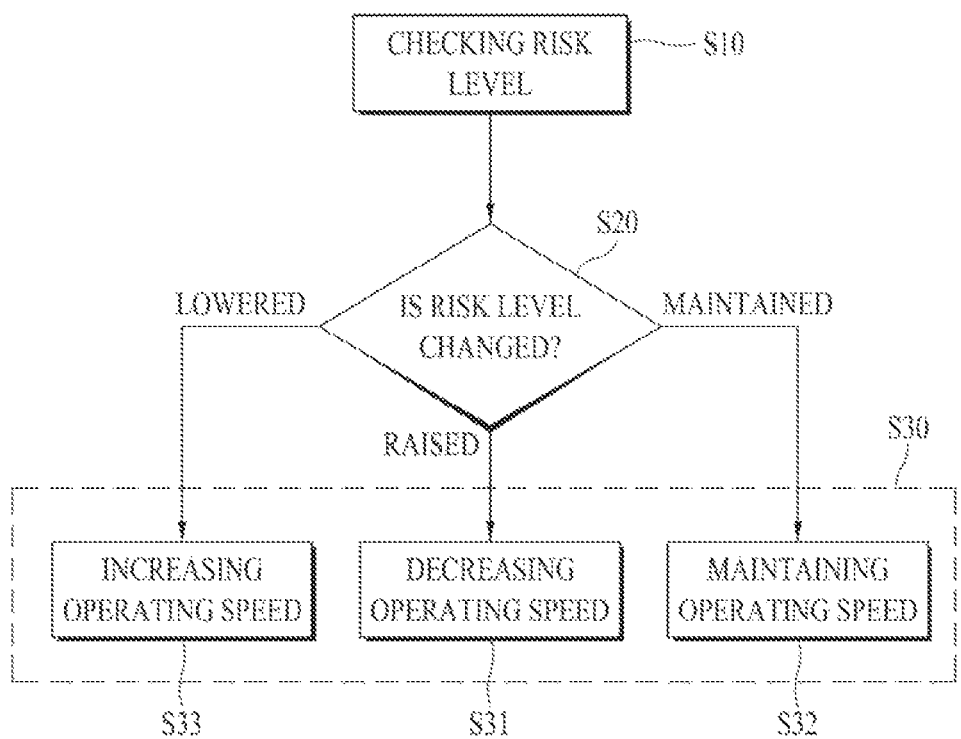
FIG. 4 is a schematic flowchart of a surgical robot control method according to an embodiment of the present invention.
Figure 5:
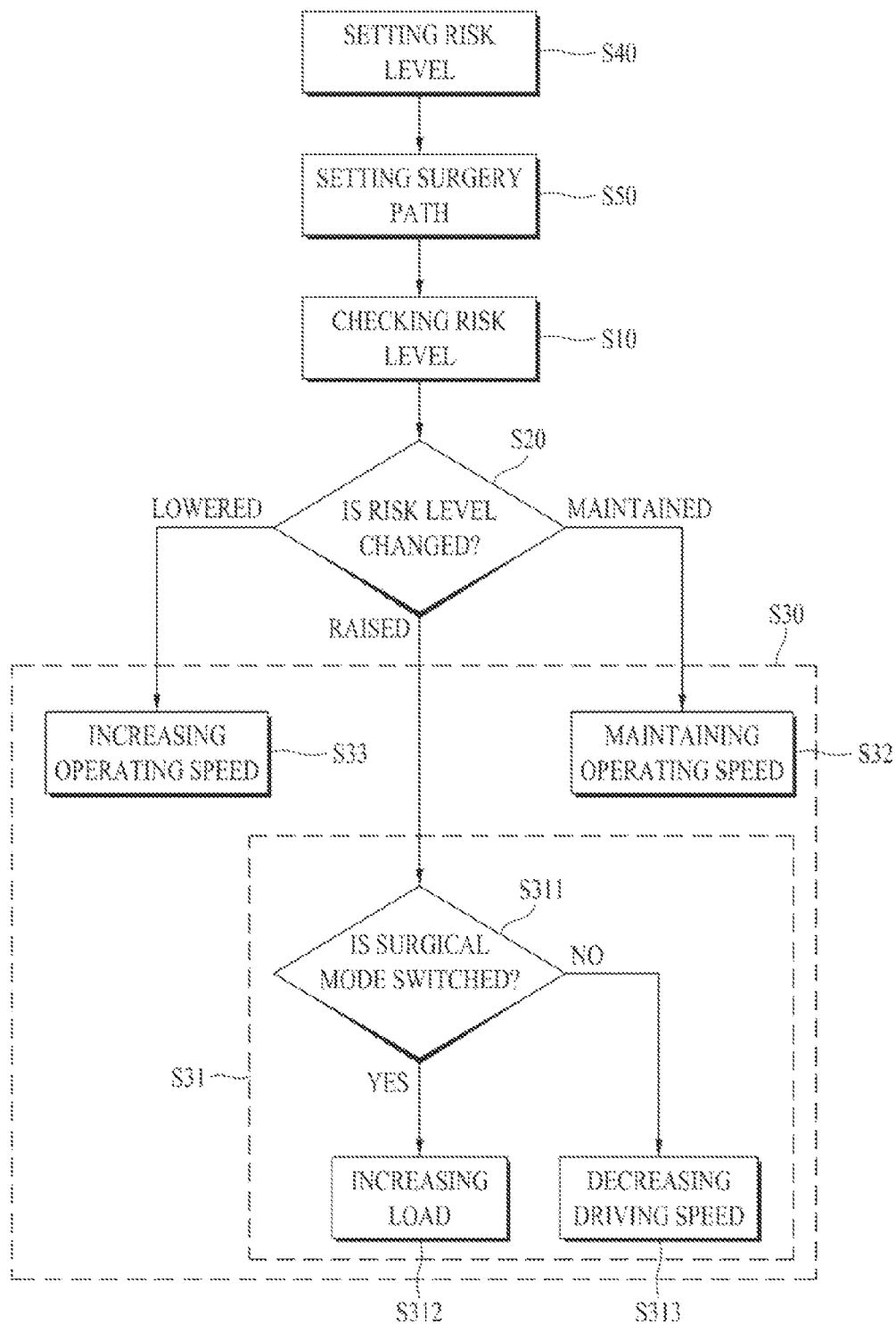
FIG. 5 is a schematic flowchart of a surgical robot control method according to a modification embodiment of the present invention.

Referring to FIGS. 1 to 3, a surgical robot system 1 according to an embodiment of the present invention performs surgery with a surgical robot 100. For example, by using the surgical robot 100, the surgical robot system 1 according to an embodiment of the present invention may perform various surgeries such as minimal invasive surgery including laparoscopic surgery, joint replacement surgery, prostatectomy, etc., based on a diseased part.

To this end, the surgical robot system 1 according to an embodiment of the present invention includes a surgical tool 110 for performing surgery on each of a plurality of procedure regions 20 dividing a surgical region 10, a robot arm 120 on which the surgical tool 110 is mounted, and a driver 130 for operating the robot arm 120 in order for surgery to be performed by the surgical tool 110. The surgical region 10 denotes a region including a diseased part. The surgical region 10 is a region including a range in which the surgical tool 110 and the robot arm 120 move for performing surgery, and may be a region which is set to have a greater size than that of the diseased part so as to surround the diseased part.

The driver 130 adjusts an operating speed at which the robot arm 120 operates, based on a risk level DL which is set for the surgical region 20 in which the surgical tool 110 is disposed. The risk level DL may be set based on a risk object 30, which is located in the surgical region 10, such as a blood vessel, an organ, or the like which exerts a great influence on a patient's life like aorta, a heart, and lungs.

For example, as illustrated in FIG. 3, a first procedure region 21 in which the risk object 30 is located may be set to a first risk level DL1 higher than a second procedure region 22 and a third procedure region 23 which are separated from the risk object 30. The second procedure region 22 next closest to the risk object 30 after the first procedure region 21 may be set to a second risk level DL2 lower than the first risk level DL1. In this case, the driver 130 may more decrease an operating speed of the robot arm 120 when the surgical tool 110 performs surgery in the first procedure region 21 than when the surgical tool 110 performs surgery in the second procedure region 22. The driver 130 may more increase the operating speed of the robot arm 120 when the surgical tool 110 performs surgery in the second procedure region 22 than when the surgical tool 110 performs surgery in the first procedure region 21.

Therefore, the surgical robot system 1 according to an embodiment of the present invention can obtain the following effects.

First, as the risk level DL which is set for the procedure region 20 in which the surgical tool 110 performs surgery becomes higher, the surgical robot system 1 according to an embodiment of the present invention decreases a speed at which the surgical tool 110 moves, thereby enhancing an accuracy, a precision, and a delicacy of the surgery performed in the procedure region 20. Therefore, the surgical robot system 1 according to an embodiment of the present invention can decrease a risk of causing a medical accident such as the surgical tool 110 contacting the risk object 30 in a process where the surgical tool 110 performs surgery in the procedure region 20 where the risk level DL is high, thereby enhancing a stability of the surgery.

Second, the surgical robot system 1 according to an embodiment of the present invention decreases a speed at which the surgical tool 110 moves in the procedure region 20 where the risk level DL is high, and thus can reduce a distance by which the surgical tool 110 is moved by inertia after the surgical robot 100 emergently stops due to the occurrence of an emergency. Therefore, when the surgical robot 100 emergently stops due to the occurrence of an emergency, the surgical robot system 1 according to an embodiment of the present invention can prevent a medical accident, such as the surgical tool 110 contacting the risk object 30, from occurring.

Third, as the risk level DL which is set for the procedure region 20 in which the surgical tool 110 performs surgery becomes higher, the surgical robot system 1 according to an embodiment of the present invention increases a speed at which the surgical tool 110 moves, and thus can shorten a time taken until the surgery is completed. Therefore, the surgical robot system 1 according to an embodiment of the present invention can enhance a stability of surgery and moreover decrease a degree to which the surgery is delayed, thereby reducing pain and inconvenience caused to an operator and a patient.

Hereinafter, the surgical tool 110, the robot arm 120, and the driver 130 will be described in detail with reference to the accompanying drawings.

Referring to FIGS. 1 to 3, the surgical tool 110 performs surgery on each of the procedure regions 20. The surgical tool 110 is operated by the robot arm 120 in a state of being inserted into a body of a patient, thereby performing surgery. The surgical tool 110 is mounted on the robot arm 120. The surgical tool 110 mounted on the robot arm 120 may be changed depending on the kind of surgery. The surgical tool 110, such as a drill, a milling, forceps, scissors, a grasper, or the like, may be mounted on the robot arm 120 depending on the kind of surgery.

Referring to FIGS. 1 to 3, the robot arm 120 is operated by the driver 130. As the robot arm 120 is operated by the driver 130, the surgical tool 110 may perform surgery on each of the procedure regions 20. The robot arm 120 may operate to move in at least one selected from a horizontal direction and a vertical direction, and thus move the surgical tool 110 in at least one selected from the horizontal direction and the vertical direction. The robot arm 120 may include a plurality of joint units which rotate with respect to different axes.

Referring to FIGS. 1 to 3, the driver 130 operates the robot arm 130. Therefore, the surgical tool 110 may perform surgery on each of the procedure regions 20. The driver 130 may adjust an operating speed at which the robot arm 120 operates, based on the risk level DL which is set for the procedure region 20 in which the surgical tool 110 is disposed.

Therefore, the driver 130 adjusts a speed at which the surgical tool 110 moves, based on the risk level DL which is set for the procedure region 20 in which the surgical tool 110 performs surgery, and thus, the surgical robot system 1 according to an embodiment of the present invention can enhance a stability of surgery which is performed by using the surgical robot 100 and moreover decrease a degree to which the surgery is delayed, thereby reducing pain and inconvenience caused to an operator and a patient.

As the risk level DL which is set for the procedure region 20 in which the surgical tool 110 performs surgery becomes higher, the driver 130 may decrease a speed at which the surgical tool 110 moves, and as the risk level DL which is set for the procedure region 20 in which the surgical tool 110 performs the surgery becomes lower, the driver 130 may increase the speed at which the surgical tool 110 moves.

For example, when the procedure regions 20 are set to be divided into three risk levels DL, the driver 130 may adjust an operating speed, at which the robot arm 120 operates, as follows.

First, when the surgical tool 110 performs surgery in the first procedure region 21, the driver 130 may operate the robot arm 120 at a first operating speed that is a lowest operating speed. The first procedure region 21 is a region which is set to the first risk level DL1 in which a degree of risk is the highest. Therefore, the surgical tool 110 may perform surgery on the first procedure region 21 while moving at a lowest speed in the first procedure region 21.

When the surgical tool 110 performs surgery in the second procedure region 22, the driver 130 may operate the robot arm 120 at a second operating speed that is faster than the first operating speed. The second procedure region 22 is a region which is set to the second risk level DL2 in which a degree of risk is lower than the first risk level DL1. Therefore, the surgical tool 110 may perform surgery on the second procedure region 22 while moving at a faster speed than the lowest speed in the second procedure region 22.

When the surgical tool 110 performs surgery in the third procedure region 23, the driver 130 may operate the robot arm 120 at a third operating speed that is a highest operating speed. The third procedure region 23 is a region which is set to a third risk level DL3 in which a degree of risk is lower than the second risk level DL2. Therefore, the surgical tool 110 may perform surgery on the third procedure region 23 while moving at a highest speed in the third procedure region 23.

Referring to FIGS. 1 to 3, the surgical robot system 1 according to an embodiment of the present invention may include a controller 200 for controlling the surgical robot 100.

The controller 200 may control the driver 130, and thus operate the robot arm 120 in order for the surgical tool 110 to perform surgery on each of the procedure regions 20. The controller 200 may supply a control signal to the surgical robot 100 by using at least one selected from wired communication and wireless communication, thereby controlling the surgical robot 100. The controller 200 may be disposed at a position which is separated from the surgical robot 100 by a certain distance. The controller 200 may be disposed to be built into the surgical robot 100.

The controller 200 may include a risk level setting unit 210.

The risk level setting unit 210 divides the surgical region 10 into the plurality of procedure regions 20, and sets the risk level DL for each of the procedure regions 20. The risk level setting unit 210 may set one of N (where N is an integer more than two) risk levels DL for each of the procedure regions 20. Hereinabove, it has been described that the risk level setting unit 210 divides the risk level DL into the three risk levels DL1 to DL3 and sets the risk level DL for each of the procedure regions 20, but the present embodiment is not limited thereto. For example, the risk level setting unit 210 may divide the risk level DL into four or more risk levels and set the risk level DL for each of the procedure regions 20.

The risk level setting unit 210 may supply the risk level DL, which is set for each of the procedure regions 20, to the driver 130. When the driver 130 receives, from the risk level setting unit 210, the risk level DL set for each of the procedure regions 20 by using at least one selected from wired communication and wireless communication, the driver 130 may adjust an operating speed at which the robot arm 120 operates, based on the received risk level DL.

The risk level setting unit 210 may set the risk level DL for each of the procedure regions 20, based on a distance by which each of the procedure regions 20 is separated from the risk object 30. For example, when the risk level DL is divided into three risk levels DL and is set for each of the procedure regions 20, the risk level setting unit 210 may set the first procedure region 21, in which the risk object 30 is located or a distance separated from the risk object 30 is 0.5 cm or less, to the first risk level DL1 in which a degree of risk is the highest. The risk level setting unit 210 may set the second procedure region 22, in which a distance separated from the risk object 30 is greater than 0.5 cm and is 1.0 cm or less, to the second risk level DL2 lower than the first risk level DL1. The risk level setting unit 210 may set the third procedure region 23, in which a distance separated from the risk object 30 is greater than 1.5 cm, to the third risk level DL3 in which a degree of risk is the lowest.

The risk level setting unit 210 may set the risk level DL for each of the procedure regions 20, based on a risk grade of the risk object 30 located within a predetermined distance for each of the procedure regions 210. The predetermined distance may be predetermined by an operator or a manufacturer. For example, when the risk level DL is divided into three risk levels DL and is set for each of the procedure regions 20, the risk level setting unit 210 may set the procedure region 20, in which a first risk object whose a risk grade is the highest is disposed within the predetermined distance, to the first risk level DL1 in which a degree of risk is the highest. The risk level setting unit 210 may set the procedure region 20, in which a second risk object having a risk grade lower than that of the first risk object is disposed within the predetermined distance, to the second risk level DL2 lower than the first risk level DL1. For example, the first risk object may be aorta which the surgical tool 110 should not contact, and the second risk object may be a liver which is possible for the surgical tool 110 to contact the liver to a certain degree. The risk level setting unit 210 may set the procedure region 20, in which a third risk object whose a risk grade is the lowest is disposed within the predetermined distance, to the third risk level DL3 in which a degree of risk is the lowest.

The risk level setting unit 210 may set the risk level DL for each of the procedure regions 20 by using a distance, by which each of the procedure regions 20 is separated from the risk object 30, and a risk grade of the risk object 30 disposed within the predetermined distance for each of the procedure regions 20. In this case, despite the procedure region 20 which is the farthest away from the risk object 30 and corresponds to the third risk level DL3, when a risk grade of a corresponding risk object 230 is high, the risk level setting unit 210 may set a corresponding procedure region 20 to the second risk level DL2 or the first risk level DL1 by raising the risk level DL. Also, despite the procedure region 20 which is the closest to the risk object 30 and corresponds to the first risk level DL1, when a risk grade of a corresponding risk object 230 is low, the risk level setting unit 210 may set a corresponding procedure region 20 to the second risk level DL2 by lowering the risk level DL.

Although not shown, the controller 200 may include a display unit for displaying the risk level DL which is set for each of the procedure regions 20 by the risk level setting unit 210. In this case, the display unit may display the procedure regions 20 in different colors, based on the risk level DL. Therefore, an operator may look at the display unit with eyes to check the risk level DL which is set for each of the procedure regions 20.

Although not shown, the controller 200 may include a storage unit that stores an image obtained by capturing a diseased part. The risk level setting unit 210 may divide the surgical region 10 into the plurality of procedure regions 20 by using the image stored in the storage unit, and set the risk level DL for each of the procedure regions 20. The image may be obtained by an imaging apparatus such as a computed tomography (CT) apparatus, a magnetic resonance imaging (MRI) apparatus, or the like. The image may be a two-dimensional (2D) image or a three-dimensional (3D) image. The storage unit may be a nonvolatile memory such as a flash memory, a hard disk, or a CD-ROM. The display unit may mark the procedure regions 20 on the image in different colors, based on the risk level DL.

Referring to FIGS. 1 to 3, the controller 200 may include a surgery path setting unit 220.

The surgery path setting unit 220 sets a surgery path, based on the risk level DL which is set for each of the procedure regions 20. The surgery path setting unit 220 may receive the risk level DL, which is set for each of the procedure regions 20, from the risk level setting unit 210 by using at least one selected from wired communication and wireless communication, and set the surgery path, based on the received risk level DL.

The surgery path setting unit 220 may set a surgery path so that surgery is performed from a procedure region 20 having a low risk level DL to a procedure region 20 having a high risk level DL. Therefore, the surgical robot system 1 according to an embodiment of the present invention first completes surgery on a procedure region 20 having a low risk level DL and then performs surgery on a procedure region 20 having a high risk level, and thus, in a state where obstacles are removed as many as possible, the surgical robot system 1 performs the surgery on the procedure region 20 having a high risk level. Therefore, the surgical robot system 1 according to an embodiment of the present invention can lower a relative surgery difficulty level when performing the surgery on the procedure region 20 having a high risk level.

Although not shown, the storage unit may store a surgery path which is set by the surgery path setting unit 220. The display unit may display the surgery path set by the surgery path setting unit 220 in order for an operator to check whether the surgery path set by the surgery path setting unit 220 is suitable. In this case, the display unit may display the surgery path by simulating surgery according to the surgery path set by the surgery path setting unit 220. When the operator changes the surgery path set by the surgery path setting unit 220, the storage unit may store the changed surgery path. The surgical robot 100 may automatically perform surgery according to the surgery path stored in the storage unit.

Referring to FIGS. 1 to 3, the controller 200 may include a change unit 230.

The change unit 230 may switch a surgery mode between an automatic mode and a collaborative mode. The automatic mode is a surgery mode in which the surgical robot 100 automatically performs surgery on the procedure region 20. When surgery on the procedure region 20 in which the surgical tool 110 is disposed is performed in the automatic mode, the surgical robot system 1 according to an embodiment of the present invention allows the surgical robot 100 to automatically perform the surgery according to the set surgery path without the operator's manipulation. The collaborative mode is a performing mode in which the operator and the surgical robot 100 collaboratively perform surgery. When surgery on the procedure region 20 in which the surgical tool 110 is disposed is performed in the collaborative mode, the surgical robot system 1 according to an embodiment of the present invention allows the surgical robot 100 to perform the surgery according to the operator's manipulation. In this case, the driver 130 may operate the robot arm 120 so that the robot arm 120 operates in correspondence with strength and a direction of a force applied by the operator.

The change unit 230 may automatically switch the surgery mode between the automatic mode and the collaborative mode, based on the risk level DL which is set for each of the procedure regions 20. For example, when the surgical tool 110 performs surgery on the second procedure region 22 set to the second risk level DL2 in the automatic mode and then moves to the first procedure region 21 set to the first risk level DL1, the change unit 230 may automatically switch the surgery mode from the collaborative mode to the automatic mode.

The change unit 230 may switch the surgery mode between the automatic mode and the collaborative mode according to an input signal provided from the operator. In this case, when a procedure region 20 in which the surgical tool 110 is disposed is changed to a procedure region 20 having a different risk level DL, the change unit 230 may display a message, which allows the operator to check whether to switch the surgery mode, in the display unit.

For example, when the surgical tool 110 performs surgery on the second procedure region 22 set to the second risk level DL2 in the automatic mode and then moves to the first procedure region 21 set to the first risk level DL1, the change unit 230 may display a message, which allows the operator to check whether to switch the surgery mode from the automatic mode to the collaborative mode, in the display unit. In this case, when the operator inputs through the display unit an input signal for switching the surgery mode, the change unit 230 may switch the surgery mode from the automatic mode to the collaborative mode.

Referring to FIGS. 1 to 3, when the surgical robot system 1 according to an embodiment of the present invention includes the change unit 230, the driver 130 may include a driving instrument 131 and a load instrument 132.

When the surgery mode is the automatic mode, the driving instrument 131 may adjust a driving speed for operating the robot arm 120. Therefore, the driver 130 may adjust an operating speed at which the robot arm 120 operates, based on the risk level DL which is set for the procedure region 20 in which the surgical tool 110 is disposed.

For example, in a case where the surgical tool 110 moves from the third procedure region 23, which is set to the third risk level DL3, to the second procedure region 22 which is set to the second risk level DL2, when the surgery mode is the automatic mode, the driving instrument 131 may decrease a rotating speed of a motor which moves the robot arm 120, thereby reducing a driving speed for operating the robot arm 120.

When the surgery mode is the collaborative mode, the load instrument 132 may adjust a load which acts in a process where the operator operates the robot arm 120. Therefore, the driver 130 may adjust an operating speed at which the robot arm 120 operates, based on the risk level DL which is set for the procedure region 20 in which the surgical tool 110 is disposed.

For example, in a case where the surgical tool 110 moves from the second procedure region 22, which is set to the second risk level DL2, to the first procedure region 21 which is set to the first risk level DL1, when the surgery mode is the collaborative mode, the load instrument 132 may change a reduction gear connected to the motor that moves the robot arm 120, thereby increasing a load which acts in a process where the operator operates the robot arm 120. Therefore, the load instrument 132 may increase a load so that a moving distance of the robot arm 120 is short and a moving speed of the robot arm 120 is slow in comparison with strength of a direction of a force applied by the operator. That is, the load instrument 132 may increase weight which the operator feels in a process where the operator moves the robot arm 120. By using a hydraulic damper equipped in the robot arm 120, the load instrument 132 may increase a load which acts in a process where the operator operates the robot arm 120.

Hereinafter, a surgical robot control method according to an embodiment of the present invention will be described in detail with reference to the accompanying drawings.

Referring to FIGS. 1 to 4, the surgical robot control method according to an embodiment of the present invention performs surgery with the surgical robot 100. The surgical robot control method according to an embodiment of the present invention may be performed by the above-described surgical robot system 1 according to an embodiment of the present invention. The surgical robot control method according to an embodiment of the present invention includes the following operations.

First, in operation S10, the surgical robot control method checks the risk level DL which is set for the procedure region 20. When the procedure region 20 in which the surgical robot 100 is disposed is changed, operation S10 may be performed by the surgical robot system 1 checking a risk level DL which is set for the changed procedure region 20. The risk level DL which is set for the procedure region 20 may be set by the risk level setting unit 210. When the procedure region 20 is changed in a process where the surgical tool 110 moves for performing surgery, the controller 200 may check the risk level DL, which is set for the changed procedure region 20, from the storage unit.

Subsequently, in operation S20, the surgical robot control method determines whether the risk level DL is changed according to the procedure region 20 being changed. Operation S20 may be performed by the surgical robot system 1 comparing a risk level DL, which is set for a before-change procedure region 20, with a risk level DL which is set for an after-change procedure region 20. Operation S20 of determining whether the risk level DL is changed may be performed by comparing a risk level DL, which is set for a procedure region 20 in which the surgical tool 110 is disposed before a change, with a risk level DL which is set for a procedure region 20 in which the surgical tool 110 is disposed after the change.

Subsequently, when whether the risk level DL is changed is determined, the surgical robot control method controls the surgical robot 100, based on the risk level DL in operation S30. Operation S30 may be performed by the surgical robot system 1 controlling the surgical robot 100 in order for an operating speed of the surgical robot 100 to be adjusted based on the risk level DL which is set for the changed procedure region 20. Operation S30 of controlling the surgical robot 100 may be performed by the driver 130 adjusting an operating speed at which the robot arm 120 operates, based on the risk level DL which is set for the changed procedure region 20.

Therefore, the surgical robot control method according to an embodiment of the present invention adjusts a speed at which the surgical tool 110 moves, based on the risk level DL which is set for the procedure region 20 in which the surgical tool 110 performs surgery, and thus can enhance a stability of surgery which is performed by using the surgical robot 100 and moreover decrease a degree to which the surgery is delayed, thereby reducing pain and inconvenience caused to an operator and a patient.

Referring to FIGS. 1 to 4, operation S30 of controlling the surgical robot 100 may further include the following operations.

First, when the risk level DL is raised as a result of determining whether the risk level DL is changed, the surgical robot control method decreases an operating speed at which the surgical robot 100 operates in operation S31. Operation S31 may be performed by the surgical robot system 1 decreasing an operating speed at which the robot arm 120 operates. Operation S31 of decreasing the operating speed at which the surgical robot 100 operates may be performed by the driver 130. For example, when the surgical tool 110 moves from the second procedure region 22, which is set to the second risk level DL2, to the first procedure region 21 which is set to the first risk level DL1, the driver 130 may decrease the operating speed at which the robot arm 120 operates.

Subsequently, when the risk level DL is maintained as a result of determining whether the risk level DL is changed, the surgical robot control method maintains the operating speed at which the surgical robot 100 operates in operation S32. Operation S32 may be performed by the surgical robot system 1 maintaining the operating speed at which the robot arm 120 operates. Operation S32 of maintaining the operating speed at which the surgical robot 100 operates may be performed by the driver 130. For example, when the surgical tool 110 moves from the second procedure region 22, which is set to the second risk level DL2, to the second procedure region 22 which is set to the second risk level DL2, the driver 130 may maintain the operating speed at which the robot arm 120 operates.

Subsequently, when the risk level DL is lowered as a result of determining whether the risk level DL is changed, the surgical robot control method increases the operating speed at which the surgical robot 100 operates in operation S33. Operation S33 may be performed by the surgical robot system 1 increasing the operating speed at which the robot arm 120 operates. Operation S33 of increasing the operating speed at which the surgical robot 100 operates may be performed by the driver 130. For example, when the surgical tool 110 moves from the second procedure region 22, which is set to the second risk level DL2, to the third procedure region 23 which is set to the third risk level DL3, the driver 130 may increase the operating speed at which the robot arm 120 operates.

Referring to FIGS. 1 to 5, operation of controlling the surgical robot 100 may further include the following operations.

First, when the risk level DL is raised as a result of determining whether the risk level DL is changed, the surgical robot control method determines whether the surgical mode is switched in operation 5311. Operation 5311 may be performed by the surgical robot system 1 determining whether the surgical mode is switched from the automatic mode to the collaborative mode. Operation 5311 of determining whether the surgical mode is switched from the automatic mode to the collaborative mode may be performed by the change unit 230.

Subsequently, when the surgical mode is switched to the collaborative mode, the surgical robot control method increases a load in operation 5312. Operation 5312 may be performed by the surgical robot system 1 increasing a load that acts in a process where the operator operates the surgical robot 100 in order for the operating speed of the surgical robot 100 to be reduced. Operation 5312 of increasing the load may be performed by the driving instrument 131.

Subsequently, when the surgical mode is maintained as the automatic mode, the surgical robot control method decreases the driving speed in operation 5313. Operation 5313 may be performed by the surgical robot system 1 decreasing the driving speed of the driver 133 in order for the operating speed of the surgical robot 100 to be reduced. Operation 5313 of decreasing the driving speed may be performed by the driving instrument 131.

Referring to FIGS. 1 to 4, the surgical robot control method according to an embodiment of the present invention may further include operation S40 of setting the risk level DL. Operation S40 of setting the risk level DL may be performed before operation S10 of checking the risk level DL which is set for the procedure region 20 is performed.

Operation S40 of setting the risk level DL may be performed by the surgical robot system 1 dividing the surgical region 10 into the plurality of procedure regions 20, and setting one of the N risk levels DL for each of the divided procedure regions 20, based on a distance by which a corresponding procedure region 20 is separated from the risk object 30. Operation S40 may be performed by the risk level setting unit 210.

Operation S40 of setting the risk level DL may be performed by the surgical robot system 1 setting one of the N risk levels DL for each of the divided procedure regions 20, based on a risk grade of the risk object 30 located within a predetermined distance. Operation S40 may be performed by the risk level setting unit 210.

Operation S40 of setting the risk level DL may be performed by the surgical robot system 1 setting the risk level DL for each of the procedure regions 20 by using a distance, by which each of the procedure regions 20 is separated from the risk object 30, and a risk grade of the risk object 30 disposed within the predetermined distance for each of the procedure regions 20. Operation S40 may be performed by the risk level setting unit 210.

Referring to FIGS. 1 to 4, the surgical robot control method according to an embodiment of the present invention may further include operation S50 of setting a surgery path.

Operation S40 of setting the surgery path may be performed by the surgical robot system 1 setting the surgery path so that surgery is performed from a procedure region 20 having a low risk level DL to a procedure region 20 having a high risk level DL. Operation S50 may be performed by the surgery path setting unit 220. Operation S50 of setting the surgery path may be performed after operation S40 of setting the risk level DL is performed. Operation S10 of checking the risk level DL which is set for the procedure region 20 may be performed after operation S50 of setting the surgery path is performed. Operation S10 of checking the risk level DL which is set for the procedure region 20 may be performed after the surgical robot system 1 starts to perform surgery with the surgical robot 100 according to the set surgery path. Operation S10 of checking the risk level DL which is set for the procedure region 20 may be performed by the controller 20 checking a risk level DL which is set for a changed procedure region 20 when the procedure region 20 is changed in a process where the surgical robot 100 performs the surgery according to the set surgery path.

As described above, the present invention adjusts a speed at which the surgical robot moves, based on a risk level which is set for a procedure region, and thus enhances a stability of surgery performed by the surgical robot and moreover decreases a degree to which the surgery is delayed, thereby reducing pain and inconvenience caused to an operator and a patient.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. A surgical robot control method comprising:
   disposing a surgical tool in a surgical region divided into a plurality of procedure regions, each of the plurality procedure regions independently having one of a first risk level, a second risk level greater than the first risk level, and a third risk level greater than the second risk level, the first, second and third risk levels being based on a risk object in the surgical region;
   moving the surgical tool from one of the procedure regions to another one of the procedure regions using a driver in the surgical robot, the other one of the procedure regions having a risk level selected from the first, second and third risk levels;
   determining the risk level of the other one of the procedure regions;
   after determining the risk level of the other one of the procedure regions, controlling an operating speed of the surgical robot based on the risk level of the other one of the procedure regions using the driver, wherein controlling the operating speed of the surgical robot comprises:
      when the risk level of the other one of the procedure regions is greater than the risk level of the one of the procedure regions, determining a surgical mode of the surgical robot, wherein the surgical mode is selected from an automatic mode in which the surgical robot automatically performs surgery, and a collaborative mode in which the surgical robot and an operator collaboratively perform surgery;
      when the surgical mode is the collaborative mode, increasing a load in a process where the operator operates the surgical tool to reduce the operating speed of the surgical robot; and
      when the surgical mode is the automatic mode, decreasing a driving speed of the driver to reduce the operating speed of the surgical robot; and
   setting a surgery path based on the risk level of each of the plurality of procedure regions using a surgery path setting unit, wherein the surgery path setting unit sets the surgery path so that surgery is first performed in any of the procedure regions having the first risk level, then any of the procedure regions having the second risk level, and then any of the procedure regions having the third risk level.

2. The surgical robot control method of claim 1, wherein controlling the operating speed of the surgical robot comprises decreasing the operating speed of the surgical robot when the risk level of the other one of the procedure regions is greater than the risk level of the one of the procedure regions.

3. The surgical robot control method of claim 1, further comprising, when the risk level of the other one of the procedure regions is identical to the risk level of the one of the procedure regions, maintaining the operating speed of the surgical robot.

4. The surgical robot control method of claim 1, further comprising:
   dividing the surgical region into the plurality of procedure regions; and
   setting one of N (where N is an integer of at least 3) risk levels for each of the procedure regions based on a distance by which a corresponding one of the procedure regions is separated from the risk object.

5. The surgical robot control method of claim 1, further comprising:
dividing the surgical region into the plurality of procedure regions; and
setting one of N (where N is an integer of at least 3) risk levels for each of the procedure regions based on a risk grade of the risk object and any other risk objects located within a predetermined distance.

6. A surgical robot system comprising:
a surgical tool configured to perform surgery on each of a plurality of procedure regions in a surgical region which is divided into the plurality of procedure regions;
a robot arm on which the surgical tool is mounted;
a driver configured to operate the robot arm, wherein the driver adjusts an operating speed at which the robot arm operates based on a risk level set for each of the plurality of procedure regions; and
a change unit configured to switch a surgical mode between an automatic mode in which surgery is automatically performed on the procedure region, and a collaborative mode in which surgery is performed on the procedure region in collaboration with an operator,
wherein the driver comprises:
a driving instrument configured to, when the surgery mode is the automatic mode, adjust a driving speed for operating the robot arm; and
a load instrument configured to, when the surgery mode is the collaborative mode, adjust a load which acts in a process where the operator operates the robot arm.

7. The surgical robot system of claim 6, further comprising a surgery path setting unit configured to set a surgery path based on a risk level which is set for each of the plurality of procedure regions,
wherein the surgery path setting unit sets a surgery path so that surgery is performed from one of the procedure regions having a low risk level to another one of the procedure regions having a high risk level.

8. The surgical robot system of claim 6, further comprising a surgery path setting unit that sets a surgery path of the surgical robot so that surgery is first performed in any of the procedure regions having a first risk level, then any of the procedure regions having a second risk level greater than the first risk level, and then any of the procedure regions having a third risk level greater than the second risk level, wherein each of the plurality of procedure regions independently has one of the first risk level, the second risk level and the third risk level, and the first, second and third risk levels are based on a risk object in the surgical region.

9. The surgical robot system of claim 8, wherein the driver reduces the operating speed of the robot arm when the risk level of the procedure region in which the surgical tool is disposed becomes higher, and increases the operating speed of the surgical tool when the risk level of the procedure region in which the surgical tool is disposed becomes lower.

10. The surgical robot system of claim 6, further comprising a risk level setting unit configured to divide the surgical region into the plurality of procedure regions, and set one of N (where N is an integer of at least 3) risk levels for each of the procedure regions, wherein the risk level setting unit sets the risk level for each of the plurality of procedure regions using a distance by which each of the plurality of procedure regions is separated from the risk object.

11. The surgical robot system of claim 6, further comprising a surgery path setting unit configured to set a surgery path, based on the risk level which is set for each of the plurality of procedure regions, wherein the surgery path setting unit sets a surgery path so that surgery is performed from a procedure region having a low risk level to a procedure region having a high risk level.

12. The surgical robot system of claim 6, further comprising a risk level setting unit configured to divide the surgical region into the plurality of procedure regions, and set one of N (where N is an integer of at least 3) risk levels for each of the procedure regions,
wherein the risk level setting unit sets the risk level for each of the plurality of procedure regions using a risk grade of the risk object and any other risk objects within a predetermined distance.

* * * * *